(12) United States Patent
Bulumulla et al.

(10) Patent No.: US 9,194,819 B2
(45) Date of Patent: Nov. 24, 2015

(54) SYSTEMS AND METHODS FOR INSPECTING REINFORCED CONCRETE STRUCTURES (71) Applicant: General Electric Company, Schenectady, NY (US)

(72) Inventors: Selaka Bandara Bulumulla, Niskayuna, NY (US); Joseph Alfred Iannotti, Glenville, NY (US); James Patrick Carneal, Wilmington, NC (US); Mahesh Panicker, Bangalore (IN)

(73) Assignee: General Electrics Company, Niskayuna, NY (US)

( * ) Notice: Subject to any disclaimer, the term of this patent is extended or adjusted under 35 U.S.C. 154(b) by 82 days.

(21) Appl. No.: 14/063,526

(22) Filed: Oct. 25, 2013

(65) Prior Publication Data

US 2015/0115980 A1 Apr. 30, 2015

(51) Int. Cl.
G01R 27/04 (2006.01)
G01N 22/02 (2006.01)
G01N 33/38 (2006.01)
G01M 7/04 (2006.01)
G01N 29/07 (2006.01)
G01N 29/265 (2006.01)

(52) U.S. Cl.
CPC ............. *G01N 22/02* (2013.01); *G01M 7/04* (2013.01); *G01N 29/07* (2013.01); *G01N 29/265* (2013.01); *G01N 33/383* (2013.01)

(58) Field of Classification Search
USPC ................................ 342/22; 702/35; 324/642
See application file for complete search history.

(56) References Cited

U.S. PATENT DOCUMENTS

| 5,541,605 | A | 7/1996 | Heger |
| 5,835,054 | A | 11/1998 | Warhus et al. |
| 5,854,492 | A | 12/1998 | Chinone et al. |
| 6,429,802 | B1 | 8/2002 | Roberts |
| 6,690,182 | B2 | 2/2004 | Kelly et al. |
| 6,772,091 | B1 | 8/2004 | Roberts |
| 7,236,120 | B2 * | 6/2007 | Healy et al. ..................... 342/22 |
| 7,548,192 | B1 | 6/2009 | Holt |
| 8,207,885 | B2 | 6/2012 | Hibbard et al. |
| 2009/0222221 | A1 * | 9/2009 | Buyukozturk et al. ......... 702/35 |
| 2010/0052971 | A1 * | 3/2010 | Amarillas ....................... 342/22 |

(Continued)

FOREIGN PATENT DOCUMENTS

JP 2007132739 A 5/2007

OTHER PUBLICATIONS

Matthew M. Andringa et al., "Unpowered Wireless Corrosion Sensor for Steel Reinforced Concrete", IEEE Sensors Conference, 2005, pp. 155-158.

(Continued)

*Primary Examiner* — Minh N Tang
(74) *Attorney, Agent, or Firm* — John P. Darling (57) ABSTRACT

An inspection system for a metal-reinforced concrete structure is described. The system includes a radio frequency (RF) system configured to be movable with respect to a surface of the concrete structure while transmitting radio signals into the interior of the structure, and receiving reflected radio signals. The system also includes a processor configured to process the reflected radio signals, so as to obtain a focused image of the reinforcement in at least one selected region within the concrete structure. The image corresponds to the physical condition of the reinforcement. A method for determining the condition of a reinforced concrete structure is also described, utilizing the inspection system.

18 Claims, 7 Drawing Sheets

(56) References Cited

U.S. PATENT DOCUMENTS

| | | | |
|---|---|---|---|
| 2011/0090110 A1 | 4/2011 | Tralshawala et al. | |
| 2012/0280849 A1 | 11/2012 | Chang et al. | |
| 2013/0018575 A1* | 1/2013 | Birken et al. | 701/409 |
| 2013/0192375 A1* | 8/2013 | Barry et al. | 73/661 |
| 2013/0220017 A1 | 8/2013 | Kim et al. | |
| 2014/0028328 A1* | 1/2014 | Kwun et al. | 324/616 |

OTHER PUBLICATIONS

Herve Abdi et al., "Principal Component Analysis", 2010 John Wiley & Sons, Inc., vol. 2, Jul./Aug. 2010, pp. 433-459.

EPRI "Robots Getting Ready to Ease Inspection of Concrete Structures", undated; web link http://www.youtube.com/ EPRIvideos, pp. 1.

Genevieve F. et al., "Imaging of Reinforced Concrete: State-of-the-Art Review", Journal of Infrastructure Systems, Jun. 1995, pp. 138-141.

Christiane Maierhofer, "Nondestructive Evaluation of Concrete Infrastructure With Ground Penetrating Radar", Journal of Materials in Civil Engineering ASCE May/Jun. 2003, pp. 287-297.

EPRI, "Program on Technology Innovation: Nondestructive Evaluation Inspection of Concrete Structures Subjected to Corrosion", Product ID: 1025627, Published May 31, 2012. Technical Report Abstract, 1 page.

Allgood et al., "Enhancing Complex System Performance Using Discrete-Event Simulation", Oak Ridge National Laboratory, 2010 Spring Simulation Multiconference, SpringSim'10. pp. 1-8.

Naus et al., "Continuing the Service of Nuclear Power Plant Civil Structures—A Review of Activities and Research Needs", 2005, Proceedings of the International Conference on Role of Concrete in Nuclear Facilities, pp. 1-12.

Naus et al., "Methods for Assessing NPP Containment Pressure Boundary Integrity", Nuclear Engineering and Design vol. 228, 2004, pp. 55-72.

Wiley., "Synthetic Aperture Radars", IEEE Transactions on Aerospace and Electronic Systems, vol. AES-21, No. 3, May 1985. pp. 440-443.

EPRI, "Enhanced Concrete Inspection of Hydropower Assets", Product ID: 1024755, Nov. 2011. pp. 1-2.

Ramo et al., "Fields and Waves in Communication Electronics", John Wiley & Sons, Second Edition 1993, pp. 283-292.

Zoughi et al., "Microwave Non-Destructive Testing and Evaluation", Kluwer Academic Publishers 2000, pp. 43-46.

European Search Report and Opinion issued in connection with corresponding EP Application No. 14189475.8 on Apr. 2, 2015.

\* cited by examiner

Synthetic aperture radar image

After removal of surface reflection

Fig. 11 Synthetic aperture image of metal tube (left), and iron oxide tube (right)

Fig. 12 Synthetic aperture image of metal plate (left), and iron oxide plate (right)

SYSTEMS AND METHODS FOR INSPECTING REINFORCED CONCRETE STRUCTURES

TECHNICAL FIELD

This invention generally relates to inspection systems. In some particular embodiments, it relates to methods for detecting the condition of reinforced concrete structures.

BACKGROUND OF THE INVENTION

Reinforced concrete is a composite material that is widely used in a number of applications. The high strength and durability of the material make it ideal for use in buildings, e.g., foundations, frames, beams, and columns; as well as walls, and other enclosures. As one example, nuclear power plants include critical structures formed of reinforced concrete, e.g., containment structures that surround a reactor vessel.

The relatively low tensile strength of concrete itself is counteracted by the inclusion of reinforcement having high tensile strength, and in some cases, greater ductility. Very often, the reinforcement is formed from steel reinforcing bars, often called "rebar". The reinforcement is usually embedded in the concrete before it sets.

One of the major drawbacks of metal-reinforced concrete is the tendency for the reinforcing bars to corrode. In general, steel has a natural tendency to corrode and return to its natural state as iron ore, e.g., ferric oxide, $Fe_2O_3$. The rate of corrosion depends on a number of factors, such as exposure to water, oxygen, and aggressive ions like chloride. Moreover, the pH and temperature of the surrounding environment, as well as the inherent properties of the steel itself, can be significant factors in the rate of corrosion. Furthermore, cracks, delamination, and voids can develop in the structures, often due to alkali-silica (alkali-aggregate) reactions that occur within the cement.

Since the degradation of the concrete reinforcement can lead to decay and collapse of concrete structures, its detection can be critical. A number of techniques exist to detect and monitor the corrosion. Visual inspection is sometimes attempted, but it can be inefficient and ineffective. Moreover, health and safety issues can be significant, e.g., if a manual inspection of a nuclear containment structure is undertaken, after the structure has been exposed to radiation.

Other methods for inspecting reinforced concrete have been used in the past. As an example, sensors have been embedded in the concrete, and attached to the rebar. While the sensors are generally able to detect the condition of the rebar, the necessity for incorporating them during the construction of the concrete structure is a distinct disadvantage in many instances.

Radio-frequency identification (RFID) sensors have also been used in this type of situation. Sensor wires or tags can be buried within the concrete. The corrosion of the sensor is expected to follow the corrosion of the iron or steel in the rebar. Again, however, these sensors must be incorporated during construction.

Another technique that has been used for this type of inspection involves an apparatus that is based on a superconducting quantum interference fluxmeter. The method is described in U.S. Pat. No. 5,854,492 (Chinone et al), and apparently is capable of the nondestructive inspection of structures that may experience defects or corrosion in metallic objects within those structures. While such a technique may be valuable in some cases, superconducting equipment usually requires sophisticated cooling systems for the conducting coils, and thus may be expensive or impractical in a number of situations.

With these considerations in mind, new techniques for inspecting metal-reinforced concrete structures would be welcome in the art. The methods should be more efficient and practical than traditional systems, e.g., being capable of use on existing structures which do not contain previously-embedded sensors. The methods should also be carried out economically, e.g., without the use of equipment that can be very expensive to operate. Moreover, it would be desirable if the methods could be capable of immediately evaluating the particular area of interest within the concrete structure, free of any interference or unwanted signal reflection from other regions of the structure.

BRIEF DESCRIPTION OF INVENTIVE EMBODIMENTS

An inspection system for a metal-reinforced concrete structure is described, comprising:
(a) a radio frequency (RF) system configured to be movable with respect to a surface of the concrete structure while transmitting radio signals into the interior of the structure, and receiving reflected radio signals; and
(b) a processor configured to process the reflected radio signals, so as to obtain a focused image of the reinforcement in at least one selected region within the concrete structure, said image corresponding to the physical condition of the reinforcement.

Another embodiment of the invention is a method for determining the condition of a reinforced concrete structure, comprising the following steps:
(i) transmitting radio signals into the interior of the structure with a radio frequency (RF) system configured to be movable with respect to a surface of the structure; and receiving reflected radio signals; and
(ii) processing the reflected radio signals, so as to obtain a focused image of the reinforcement in at least one selected region within the concrete structure, said image corresponding to the physical condition of the reinforcement.

DETAILED DESCRIPTION

When introducing elements of various embodiments of the present invention, the articles "a," "an," "the," and "said" are intended to mean that there are one or more of the elements, unless otherwise indicated. Moreover, the terms "comprising," "including," and "having" are intended to be inclusive, and mean that there may be additional elements other than the listed elements. As used herein, the term "and/or" includes any and all combinations of one or more of the associated listed items. Furthermore, unless otherwise indicated herein, the terms "disposed on", "deposited on" or "disposed between" refer to both direct contact between layers, objects, and the like, or indirect contact, e.g., having intervening layers therebetween.

Approximating language, as used herein throughout the specification and claims, may be applied to modify any quantitative representation that could permissibly vary without resulting in a change in the basic function to which it may be related. Accordingly, a value modified by a term such as "about" is not limited to the precise value specified. In some instances, the approximating language may correspond to the precision of an instrument for measuring the value.

As mentioned previously, embodiments of this invention are directed to the inspection of reinforced concrete. Concrete is usually formed as a mixture of coarse stone or brick chips, with fine aggregates, such as sand or crushed stone. A binder is also present, e.g., a hydraulic cement such as Portland cement. When mixed with a small amount of water, the cement usually hydrates to form microscopic opaque crystal lattices, encapsulating and locking the aggregate into a rigid structure.

The thickness of the cement structure can vary greatly, depending on its end use. For many (though not all) embodiments of the present invention, the thickness will be in the range of about 5 cm to about 1 meter. In some specific embodiments, the range will be from about 80 cm to about 1 meter.

The reinforcement in the concrete is usually steel or iron reinforcing bars. The bars (e.g., rebar) are typically embedded passively into the concrete, before it sets. The bars can be arranged in a variety of layers and patterns, e.g., single or double reinforcement. Moreover, the bars are usually situated in a region of about 20% to about 80% of the thickness of the concrete structure. In some cases, the concrete structure may be reinforced near what is termed a "tensile face"; while in other cases, the reinforcement may be located in what is termed a "compressive" face. (Reinforcement can be in both locations as well).

As mentioned above, a radar system is used to transmit and receive radio waves/pulses from the interior of the concrete structure. As those skilled in the art understand, the system involves sending radio frequency signals into the structure. Continuous modes or pulsed modes can be used, although a pulsed mode is sometimes preferred. As further illustrated below, the system usually includes at least one antenna proximate to the surface of the concrete structure, capable of transmitting radio signals, and receiving reflected radio signals.

In general terms, a radar system suitable for embodiments of this invention often (but not always) includes:

a transmitter that generates the radio signal, usually with some type of oscillator (e.g., a magnetron or klystron). The transmitter also typically includes a modulator that controls the duration and/or frequency of the radio signal;

a waveguide that links the transmitter and the antenna;

a duplexer that functions as a switch between the antenna and the transmitter, or receiver, in those situations in which the antenna is used for both situations;

a receiver and an analog-to-digital converter;

a display processor for processing the reflected radio signals, producing corresponding signals that are readable to an operator;

an electronic platform, in various forms, that controls all of the above devices, as well as at least one antenna, and thereby allows the scan that is ordered by a software system; and an electronic link to all operator devices and displays.

In one illustrative embodiment, a radar apparatus typically generates a pulse signal for modulation by using a pulse generator. The generator emits a modulation pulse modulated by a high frequency wave toward the selected surface of the concrete structure, via a transmitting antenna. A receiving antenna that is also associated with the radar system receives a wave that is reflected by the reinforcement in the structure, toward which the modulated pulse had been emitted. Usually, the received signal is then amplified and de-modulated, outputting a base-band that can effectively be translated into an image that corresponds to the physical condition of the reinforcement.

In another embodiment, a continuous wave radar apparatus generates a sinusoidal signal of a specific frequency. The generator emits the signal toward the selected surface of the concrete structure, via a transmitting antenna. A receiving antenna that is also associated with the radar system receives a wave that is reflected by the reinforcement in the structure, toward which the signal had been emitted. The frequency of the signal is next increased, and the process is repeated. The amplitude and phase of received signals are ordered according to the frequency of the generated signal. (The frequency bandwidth of the continuous wave radar system is often in the range of about 1.7 gigahertz (GHz) to about 2.1 gigahertz (GHz)). An inverse Fourier transform can be performed to obtain a time domain signal.

Figure 1:
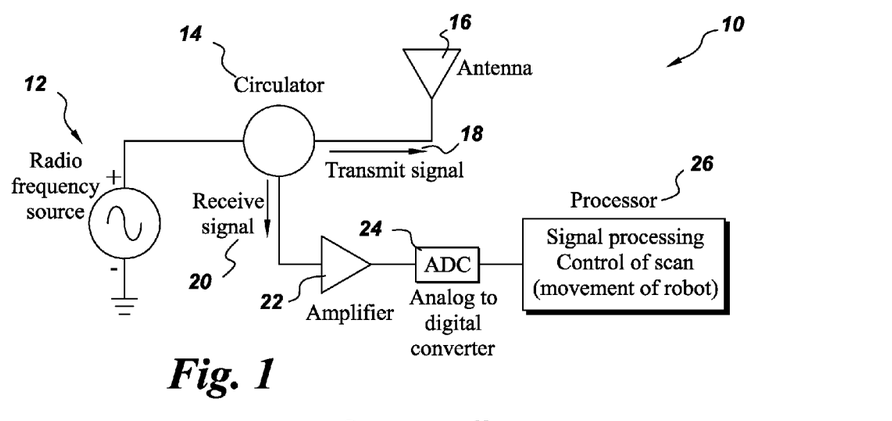
FIG. 1 is a schematic representation of an inspection system according to some embodiments of this invention.

FIG. 1 is a depiction of one exemplary RF system 10. The system includes any suitable type of radio frequency source 12, communicating with a circulator 14. The antenna 16 is connected to circulator 14, and transfers the radio frequency signal 18 into the concrete structure (not shown in this figure). A receiver 20 (not specifically shown) receives the signal(s) reflected from the concrete structure, while an optional amplifier 22 strengthens the signal. An analog-to-digital converter 24 can be used to convert the reflected signals to digital form, to enable automated processing of the signals. As alluded to previously, a processor 26 processes the reflected radio signals, while also controlling the movement of a vehicle or robot (not shown here, but described below) that can physically support most or all of the system components.

Figure 2:
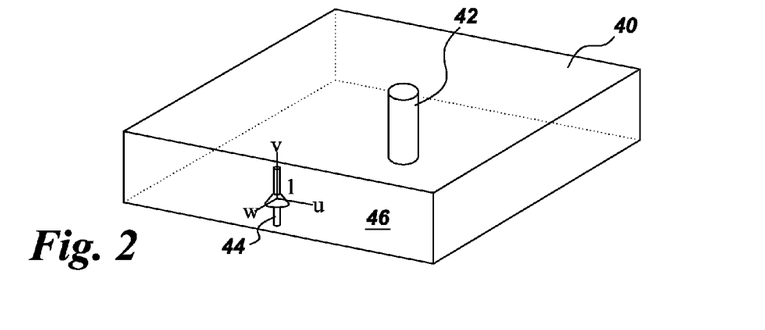
FIG. 2 is a schematic representation of a concrete structure in which reinforcement is embedded.

FIG. 2 is a simple illustration of a portion of the inspection system for embodiments of this invention, as used for monitoring any type of concrete structure 40. The structure can include various types of reinforcement structures, illustrated, for simplicity, as a single rebar section 42. As mentioned earlier, an antenna 44, is configured to transfer the radio frequency signal into the concrete; and then to receive the reflection of the signal, for further processing. The antenna, situated on or adjacent to a selected surface 46 of the structure, can be manually or automatically moved across the surface.

Figure 3:
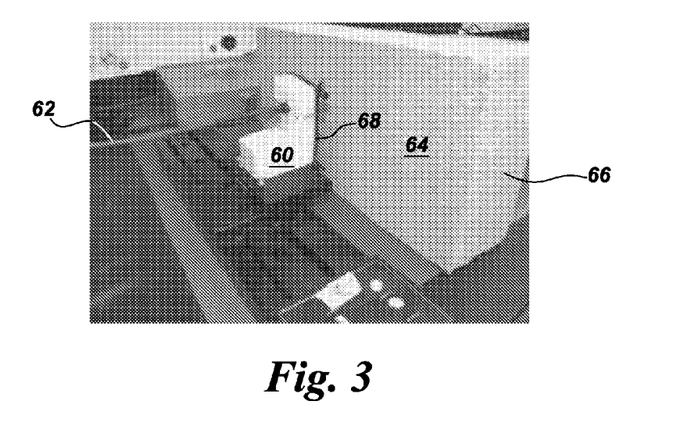
FIG. 3 is a photograph of an inspection system adjacent a sample concrete structure.

As mentioned above, most components of the inspection system, or the entire system, is configured to be movable, on or adjacent to a surface of the structure under inspection. In simplified form, FIG. 3 generally illustrates the concept. A radio signal system/processor unit 60 can be moved by any suitable type of machine-controlled shaft support 62, along the surface 64 of a concrete structure 66. Unit 60 includes an antenna 68, as discussed above, that is capable of transmitting the necessary signals into surface 64, and receiving the reflected signals for processing. The technique of using a mobile antenna to obtain multiple readings of the reflected signals is sometimes referred to as the synthetic aperture technique (SAR).

A variety of different techniques can be used to allow movement of the inspection system. The system could be fixed to a platform that includes wheels to move along a concrete surface. Cables or some type of guide bars could be used to push or pull the system in the desired direction, e.g., across a length of the surface, or up and down the surface. As the inspection system moves along the surface, it generates a profile of the condition of the reinforcement and surrounding concrete at a selected depth, as further described herein. Care should be taken to properly align the antenna with the surface being inspected, so that maximum signal strength can be obtained during transmission and reflection.

Alternatively, tracks or other types of rails could be fixed to the surface, or adjacent the surface, and could support the inspection system. In some embodiments, the tracks would be formed of a material that is non-magnetic, and/or not electrically conductive. The system could also be fixed to a platform (e.g., mechanically, or with suction cups or the like) which moves along the tracks in a desired direction or pattern— usually a pre-programmed pattern.

In other embodiments, various types of robotic devices could be used, moving along the surface while being secured by one of the techniques described above. The robot in which the inspection system is contained could be self-guided by a computer program and internal circuitry, moving along a pre-selected grid, usually under its own power system. The use of robots for inspecting concrete structures has been disclosed by the Electric Power Research Institute.

It should be noted that the entire inspection system need not be situated on a moveable platform. For example, the antenna (or multiple antennae) could be situated on, or attached to, the platform, along with associated devices. The other components of the system could be located nearby, in a stationary position that might include a docking station. When the inspection of a particular grid is complete, the moveable platform could return to the docking station, for the downloading of data, and/or recharging of power systems. (In other embodiments, data could be continuously transmitted to a docking station or other processing station by suitable types of wireless transmission).

Figure 4:
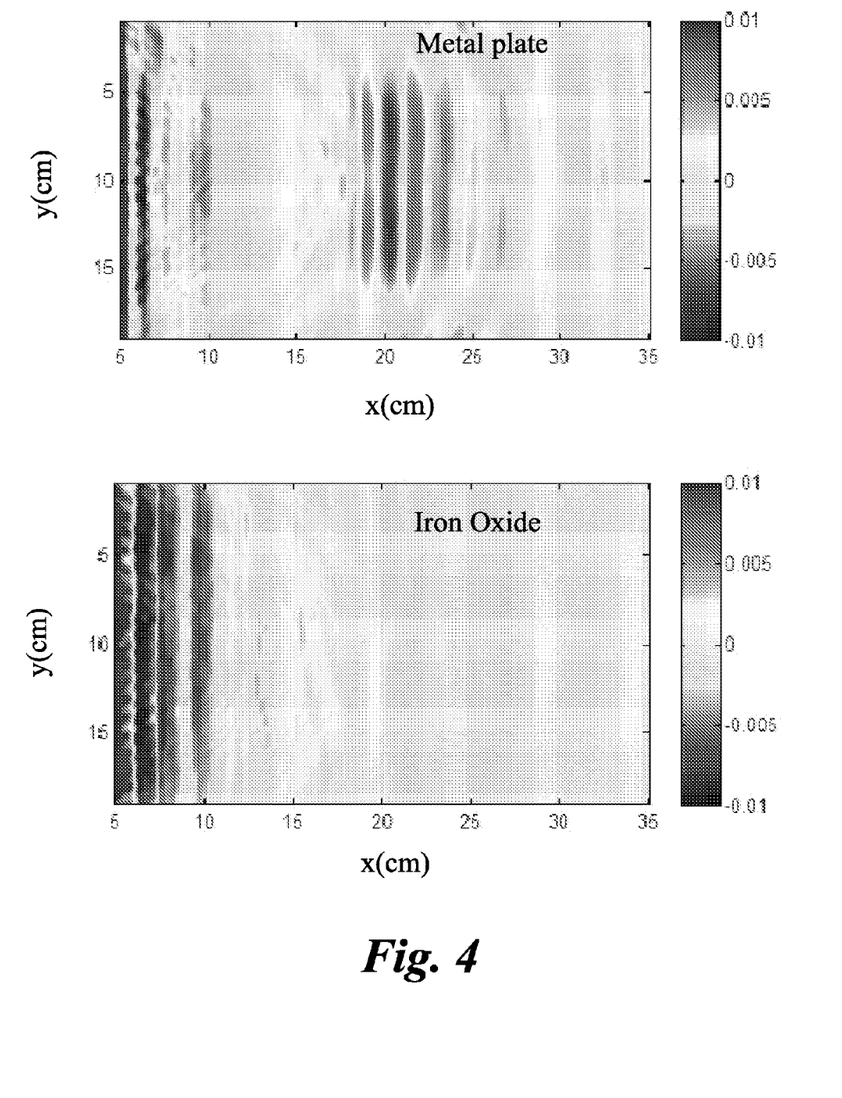
FIG. 4 is a set of radar images for concrete structures examined according to embodiments of this invention.

FIG. 4 is a depiction of two radar images for illustrative concrete structures that can be examined according to embodiments of this invention. The top figure relates to a concrete sample with an embedded plate formed of steel, representing reinforcement that is in an acceptable condition. The bottom figure is a concrete sample in which a cavity of similar volume and location is filled with iron oxide (black rust). Each structure was analyzed with an inspection system as described herein. (Additional details are provided in the Examples below).

In each figure, the X-axis (horizontal axis) represents depth into the concrete, from a selected surface. The Y-axis (vertical axis) represents the scan direction. (The figures can also be generated in color, for maximum differentiation of the features. The bar on the right of each individual figure shows the intensity of the reflected radio signals). The relatively strong reflection signals in the 18-22 cm range in the top figure are an indicator of the presence of elemental metal, i.e., reinforcement that is in good condition. The absence of such signals in approximately the same region for the bottom figure is an indication of the absence of elemental metal and the presence of metal oxide, i.e., iron oxide (rust) or other deterioration.

Figure 5:
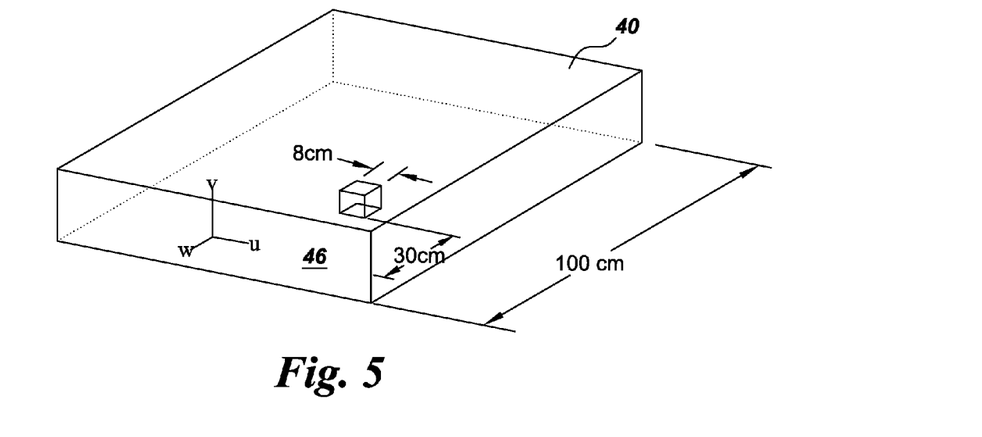
FIG. 5 is a schematic representation of a cavity situated within a sample concrete structure.

Moreover, a distinctive image is also apparent in those cases in which a void, i.e., any type of cavity, is present in the bulk of the cement. Thus, the inspection system can be used to check for that type of phenomenon as well. FIG. 5 is an illustration of a cavity within a 1 meter-thick concrete sample. The cavity has dimensions of 8 cm×8 cm×8 cm. The cavity was positioned 30 cm from the inspection face of the concrete block (see the direction arrow in the figure).

Figure 6:
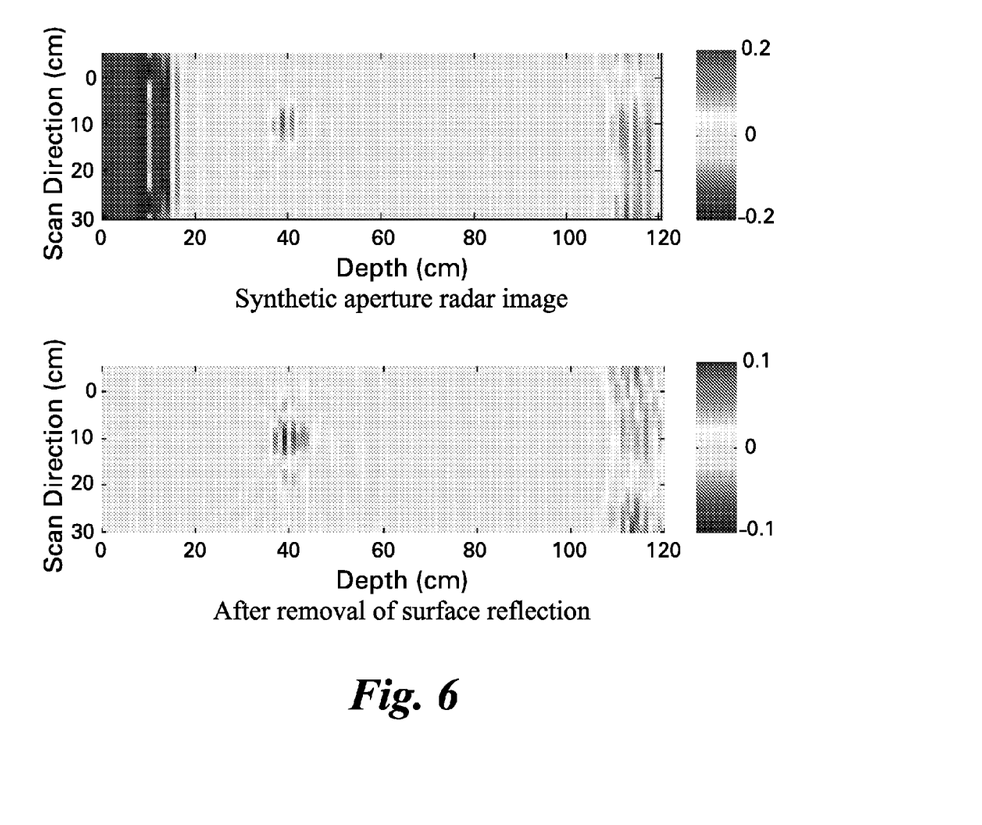
FIG. 6 is a set of radar images for the cavity illustrated in FIG. 5, after an inspection process.

FIG. 6 includes two images for the void illustrated in FIG. 5, after inspection according to the process outlined herein, i.e., using the synthetic aperture radar technique. The top image, showing scan direction as a function of depth, shows the presence of the void. The bottom image is also based on scan direction as a function of depth, and shows the location of the void after removal of surface reflections, as described below.

When a radio frequency signal is transmitted to the concrete structure, the signal is reflected back at the boundary of the structure material. The first material boundary that is encountered is the air/concrete interface. The radio frequency signal is partially reflected at this interface. The remaining signal is transmitted into the structure. The signal transmitted into the structure is later reflected by the concrete/metal interface, e.g., the rebar.

The reflected signal of interest is the signal from the concrete/metal interface. However, due to attenuation of the signal during transmission through concrete, the amplitude of this signal is lower. The first reflected signal from the air/concrete interface has a much higher amplitude, because it did not travel through an attenuating medium such as concrete. As a result, the signal of interest will be more difficult to detect, due to the higher amplitude surface reflection.

The reflections from a region that is closer to a scan-surface may get "buried" in the surface reflection. In order to avoid this occurrence, the surface reflection is removed through signal processing methods, as described below. The two figures of FIG. 6 show the reconstructed sub-surface image, prior to removal of surface reflection (top), and the image after removal of surface reflection (bottom).

In some embodiments, an additional processing step is undertaken, to process the reflected radio signals that result from use of the RF inspection system. As mentioned above, the step is designed to address very strong reflected signals that are produced at the outer surfaces of the concrete structure, e.g., in the vicinity of surface 46 in FIG. 2, which is closest to antenna 44. In the absence of compensation for the signal strength in this air/concrete interface, defects in the structure can sometimes be hidden.

The additional processing step usually involves principal component analysis (PCA). This technique can effectively remove signal components that correspond to strong reflections from the surface region. PCA is known in the art as a mathematical procedure that usually employs orthogonal transformation to convert a set of observations of possibly correlated variables into a set of values of linearly uncorrelated variables, referred to as "principal components". In this manner, important information from a data table (such as a set of reflected radio signal data points) can be extracted and expressed with a new set of variables that provide a more accurate reading of the entire set of data. PCA is described, for example, in "Principal Component Analysis", Volume 2, July/August 2010 (John Wiley and Sons), pp. 433-459, which is incorporated herein by reference. Aspects of principal component analysis are sometimes referred to as "singular value decomposition".

In some specific embodiments that use the PCA process, multiple radio signals or waveforms are first analyzed. All of the waveforms have a common waveform that is independent of the first reflection, i.e., the outer surface reflection. The common waveform is determined, and then separated from all of the other waveforms. In this manner, the strong signal at the surface of the structure is effectively minimized or eliminated.

Figure 7:
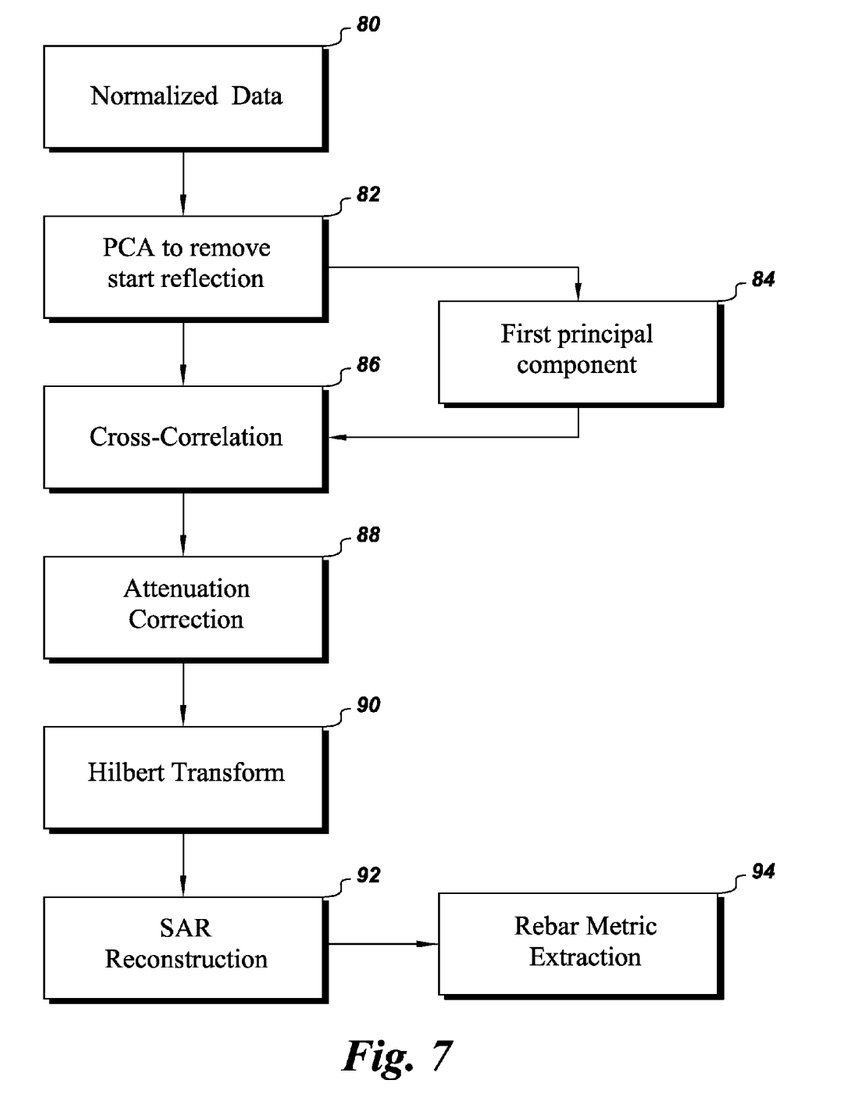
FIG. 7 is a block diagram representation of radar signal processing steps according to inventive embodiments.

The following steps are a non-limiting illustration of one particular technique for processing the reflected radio signals obtained from the inspection of a concrete structure containing reinforcement. The general, illustrative sequence is also depicted in FIG. 7.

Reflected Radio Signal Processing

1. Normalize each waveform for unity amplitude (Step 80 of FIG. 7);
2. Perform principal component analysis (PCA), so as to remove the reflection from the first interface (air/concrete) (Step 82);
3. Obtain first principal component (representative of transmit signal) (Steps 82, 84);
4. Use first principal component in filtering each waveform (cross-correlation step 86);
5. Use the estimated signal attenuation of radio frequency signals in concrete to increase amplitude of the signals, based on the propagation delay (attenuation correction step 88);
6. Create an analytical signal for each waveform by performing a Hilbert transform of each waveform (Step 90);
7. Use the magnitude of the waveforms and back-projection algorithm to generate a sub-surface image of concrete (Step 92);
8. Project this 2D image to the scan direction by estimating the maximum value at each scan location, using the SAR technique (Step 92 also);
9. Use this information to estimate reflection amplitude (amplitude metric)
10. For identified peak location, plot phase of analytical signal for reflected waveform;
11. Estimate slope of phase using phase values of analytical signal prior to rebar, and after rebar; and
12. Use amplitude metric and phase metric to predict condition of rebar (Step 94).

Figure 8:
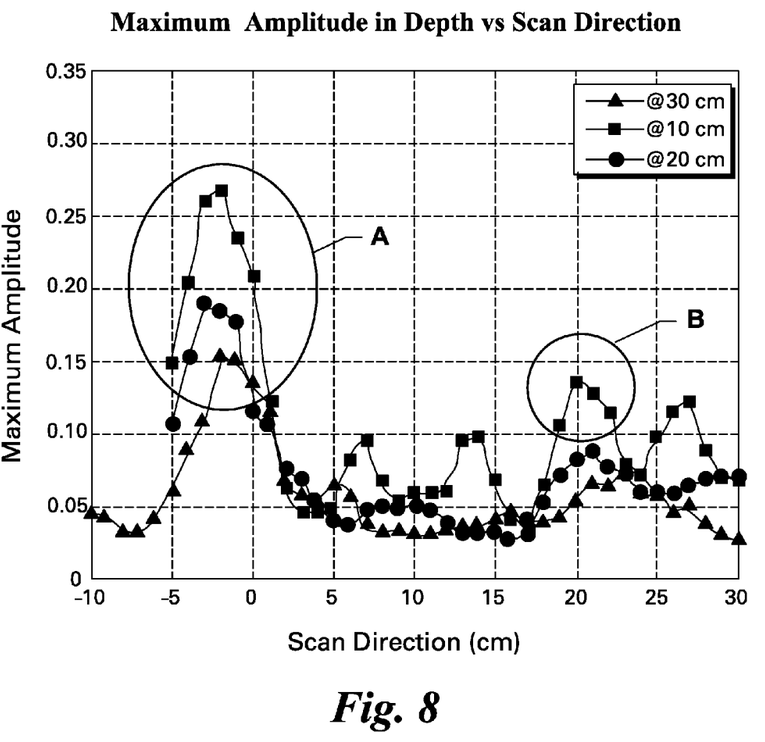
FIG. 8 is an image based on radar inspection data for a reinforced concrete structure.

FIG. 8 is an image based on radar inspection data for a concrete structure with rebar-type reinforcement, corrected after using PCA to properly evaluate the data set of reflected radio signals. The vertical axis represents the maximum amplitude of the reflected radio signals, at three different distances within the concrete structure—10 cm, 20 cm, and 30 cm. The horizontal axis represents the scan direction. Circle "A" has been inserted to clearly show the region of highest signal amplitude, which is an indication that the rebar is intact and in good condition in the region of interest within the structure. Circle "B" has been inserted to show the location of corroded rebar (represented by a cylinder of iron oxide material in the model). The amplitude at this location is much lower than the amplitude for the intact rebar.

Additional embodiments of this invention relate to techniques for quantifying and more simply expressing the condition of the reinforcement in the concrete structure. A reinforcement or rebar "health metric" can be established, based on the primary inspection system described above, with optional use of the PCA technique. In general, the reflected radio signals from the structure represent a reflected signal amplitude from a rebar of interest, which can be processed, using a phase slope adjacent or near the rebar, to provide the health metric.

In some specific embodiments, the health metric is based on the following factors, discussed previously:

Function(amplitude,shape, de/d0)

In calculating the metric with an appropriate algorithm, the signal amplitude usually should be corrected for signal attenuation, which can be dependent on factors like moisture levels, and signal depth within the structure. The "shape" variable is a correlation with the waveform that is expected to be generated from the specific type of reinforcement. The "d0" value is determined by the original dimension of the reinforcement. (For example, rebar shape, size, and location within a structure is very often known beforehand, according to construction specifications). The "de" value is the estimated dimension for the reinforcement, e.g., the diameter of conventional steel bars that are used to form rebar. The algorithm mentioned above also can be used to calculate the slope of the reflected signal phase closest to the reinforcement feature that is being inspected, which is a quantity that can also be used in the calculation of the metric. In general, a higher metric value should be indicative of better condition for the reinforcement. A lower metric value should be indicative of damage (e.g., corrosion) within the reinforcement.

Figure 9:
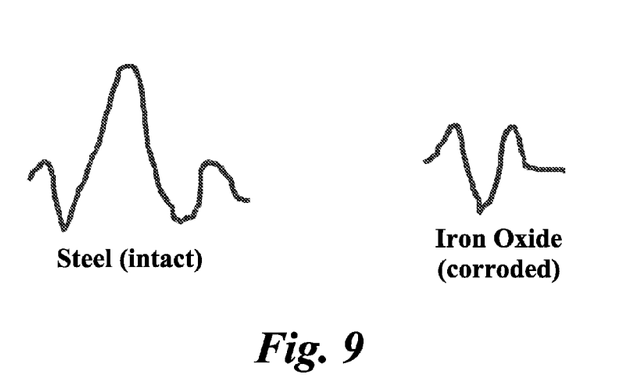
FIG. 9 is a graphical depiction of reflected signal phases for concrete samples examined according to the inspection system.

FIG. 9 is a simplified graphical depiction of reflected signal phases (showing a phase inversion) for two concrete samples examined for the condition of rebar embedded therein. In each instance, a comparison of reflected signal amplitude was used to determine the rebar health metric. The figure on the left shows a higher amplitude with a waveform shape having a dominant peak, indicating the presence of steel, i.e., intact rebar. The figure on the right shows an inverted waveform shape with a dominant "valley", indicating the presence of iron oxide, i.e., corroded reinforcement.

Figure 10:
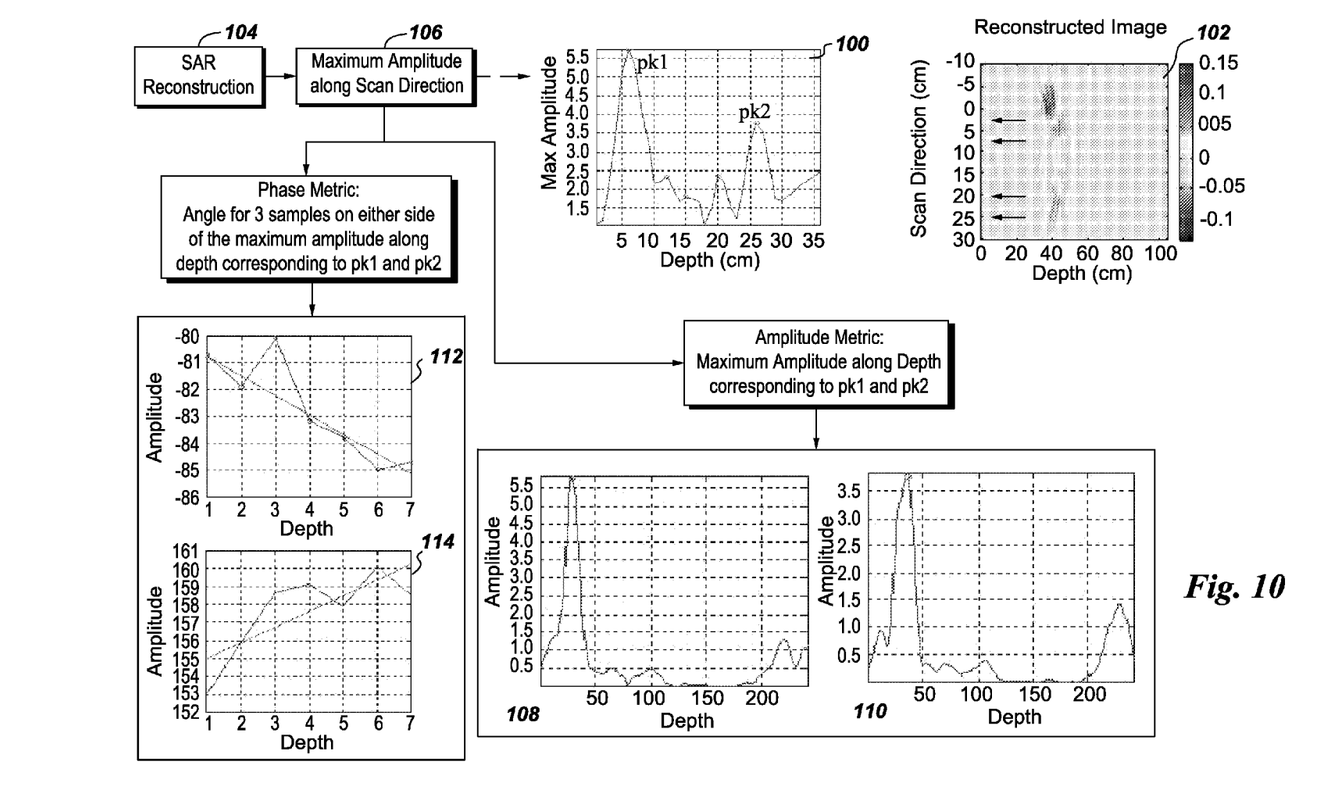
FIG. 10 is an illustration of data extraction for determining the condition of reinforced concrete, according to the inspection system.

The health metric of the reinforcement in concrete, using an appropriate algorithm, can be expressed in quantities that represent a comparison of phase amplitude, for the reflected radio signals. FIG. 10 is a simple illustration for the extraction of data to obtain a suitable health metric, according to one embodiment. A one-dimensional plot 100 is obtained by using a two-dimensional image 102, obtained after processing the reflected radio signals, as described herein, and showing a reconstructed image which includes a plot of depth as a function of scan-direction. For the image 102, the maximum value for a given row to a scan location is provided. The arrows added to the image indicate the calculation of the maximum value for a given row. Those maximum values are used to construct plot 100. The data obtained in the scans was processed, in step 104, based on the use of the SAR technique and subsystem mentioned previously. The technique provides an estimate 106 of the maximum amplitude along a selected scan direction, which is also used to construct plot 100. Plot 100 shows two distinct peaks, pk1 and pk2, representing the amplitude of the reflected signals from intact rebar, and from corroded rebar.

With continued reference to FIG. 10, the amplitude metric that is further discussed below is taken as a maximum amplitude value through the depth of the concrete structure, corresponding to the two peak values, pk1 and k2, as shown in graphs 108 and 110, respectively. The phase metric is calculated from three samples on either side of the maximum amplitude values, along the depth corresponding to the peaks, pk1 and pk2. Graphs 112 and 114 represent the extraction of the data for peaks pk1 and pk2, respectively.

Table 1 compares the amplitude for sample bars formed of steel and iron oxide:

TABLE 1

Reinforcement Health Metric - Amplitude Comparison

| Depth (Bar Diameter) | Steel Bar | Corroded Iron Oxide Bar |
|---|---|---|
| 10 cm-2.5 cm | 0.3307 | 0.1473 |
| 20 cm-2.5 cm | 0.1961 | 0.1065 |
| 30 cm-2.5 cm | 0.1529 | 0.0754 |
| 20 cm-3.5 cm | 0.2232 | 0.0839 |

Table 1 shows that numerical values based on the health metric can be used to very readily determine the condition of the concrete reinforcement. Higher amplitude values at each depth within the concrete structure are shown for the steel material, as compared to the corroded iron oxide material.

The health metric of the reinforcement in concrete can also be expressed in terms of phase values. Table 2 is instructive:

TABLE 2

Reinforcement Health Metric - PhaseValues

| Depth (Bar Diameter) | Steel Bar | Corroded Iron Oxide Bar |
|---|---|---|
| 10 cm-2.5 cm | −80.0549 | 154.105 |
| 20 cm-2.5 cm | −106.887 | 137.525 |
| 30 cm-2.5 cm | −163.106 | 65.562 |
| 20 cm-3.5 cm | −112.007 | 129.7861 |

Table 2 shows that the phase values (the slope of the phase near the location of the rebar) can also be used as a numerical indicator for the condition of the reinforcement. Negative values are consistently present for the steel bars; while positive values are consistently present for the corroded iron oxide bars, which represent corroded reinforcement materials.

EXAMPLES

The examples that follow are merely illustrative, and should not be construed to be any sort of limitation on the scope of the claimed invention.

Three antennas were designed for experimental data collection, in relation to an inspection system as described previously. All three antennas were designed as dipole antennas, for easy fabrication. The lengths of the antennas and the resonant frequencies when placed next to a concrete structure were as follows:

TABLE 3

| | Length | Resonant Frequency |
|---|---|---|
| Antenna 1 | 5.3 cm | 2.083 GHz |
| Antenna 2 | 2.6 cm | 5.23 GHz |
| Antenna 3 | 6.5 cm | 1.796 GHz |

The return-loss characteristics for each antenna were also measured.

Concrete samples were prepared using Quickrete™ mortar mix. The mortar mix was poured into a plastic mold having dimensions of about 28 cm×33 cm×6 cm. According to the general illustration of FIG. 2, described above, a steel plate having a size of 12.5 cm×4.5 cm×0.99 mm was placed vertically, approximately 20 cm from one end of the mold. The sample was cured at room temperature, and then further dried in an oven. An identical sample was prepared with the metal plate replaced with a plastic plate. Following sample curing, this plastic piece was removed and filled with iron oxide.

A third sample was prepared with a metal tube embedded in the concrete. The metal tube was 2.5 cm in diameter, and 5 cm in height. An identical sample was prepared with the metal tube replaced by a Plexiglas™ tube of similar diameter and height. Following curing of the sample, the tube was filled with iron oxide (Fisher Scientific, Laboratory grade black powder).

Using all three antennas, reflection data from the concrete samples were collected, using an Agilent N5230A Network Analyzer. The network analyzer typically operates in the selected frequency domain, producing return-loss (S11) data. The network analyzer was operated in a "transform" mode, to obtain time domain reflection coefficients. In this mode, the network analyzer acquires data in the frequency domain, and then performs a Fourier transform to generate time domain waveforms. The data collection was carried out by placing the antenna on the concrete block face, and acquiring data at 1 cm intervals. The "transmit" power levels used in the experiments ranged from 0-5 dBm (1-3.16 mW). The data for the concrete sample with the metal plate were analyzed. The 2.083 GHz antenna appeared to provide the clearest data, of the three antennas. It was used for the remainder of the experiments.

In order to obtain improved images of the embedded objects, synthetic aperture techniques were used to post-process the reflection data. This was done off-line, using Matlab™ software. The software was modified to read-in network analyzer data, and to process time domain waveforms, assuming a dielectric constant of 6, for concrete. The results are then plotted as a function of depth, so that the location of the object can be identified, in addition to the shape and approximate dimensions.

Figure 11:
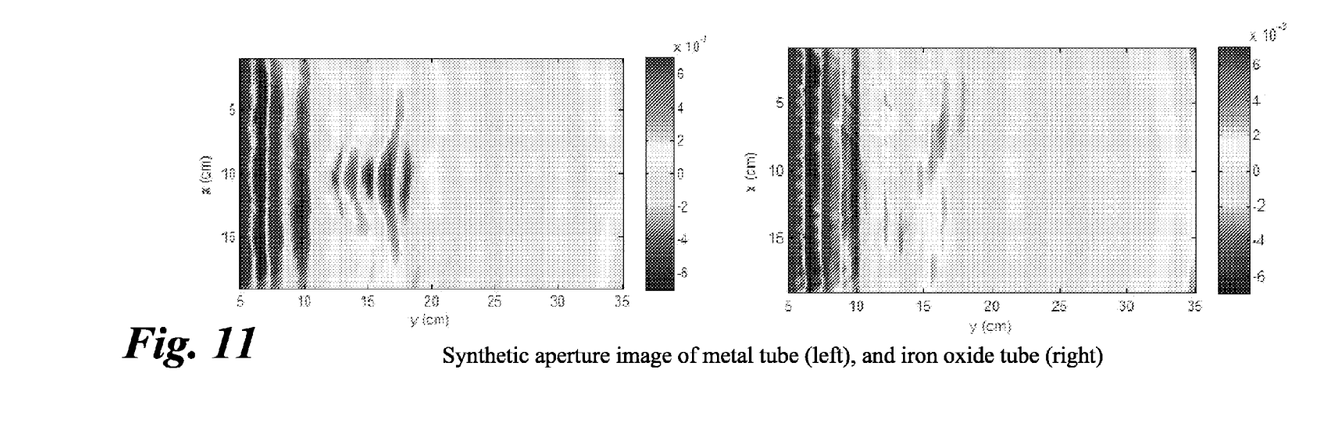
FIG. 11 is a set of synthetic aperture images for different features within a sample concrete structure.

The results of the metal tube, and a similar volume filled with iron oxide, are shown in the synthetic aperture image of FIG. 11. As seen in the figure, the metal tube is clearly identifiable from the reflection data. However, for the sample with iron oxide, a similar identification cannot be made.

Figure 12:
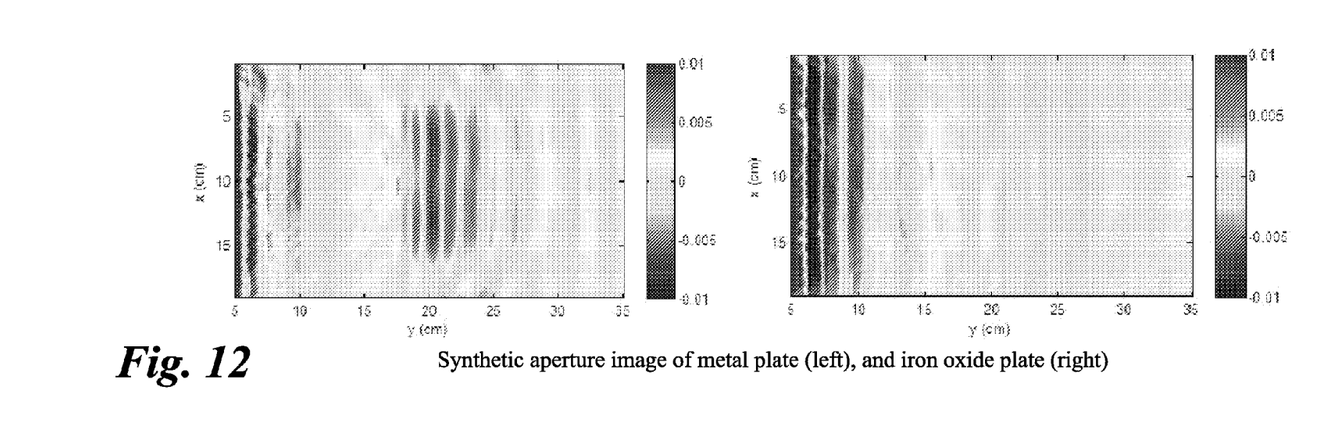
FIG. 12 is another set of synthetic aperture images for selected features within a sample concrete structure.

FIG. 12 is also a synthetic aperture image, for the sample that included the metal plate, as compared to the sample having a similar volume filled with iron oxide. As seen in the figure, the metal plate is clearly identifiable. However, for the sample filled with iron oxide, the reflections have a lower amplitude, leading to a diffused image. In each instance, the ability to inspect reinforced concrete and detect its condition has been clearly demonstrated.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed:

1. An inspection system for a metal-reinforced concrete structure, comprising:
    (a) a radio frequency (RF) system configured to be movable with respect to a surface of the concrete structure in a scan direction, transmit radio signals into the interior of the structure at a plurality of scan locations, and receive reflected radio signals; and
    (b) a processor configured to process the reflected radio signals by:
        normalizing each waveform of the reflected radio signals for unity amplitude, performing a principal component analysis to remove a first reflection from a first interface of the radio signals to the metal-reinforced concrete structure, obtaining a first principal component representative of the transmitted radio signals and using the first principal component to filter each waveform, correcting attenuation of the radio signals in the metal-reinforced, concrete structure, creating an analytical signal for each waveform, generating a sub-surface 2D image of the metal-reinforced concrete structure using the magnitude of the waveforms, projecting the 2D image to the scan direction by estimating a maximum value at each scan location to estimate reflection amplitude, for each identified peak location, plotting a phase for each waveform, and estimating a slope of the phase prior to and after a metal-reinforcement, wherein the slope corresponds to the physical condition of the metal-reinforcement.

2. The inspection system of claim 1, wherein the RF system includes at least one antenna configured to transmit the radio signals and receive the reflected radio signals.

3. The inspection system of claim 1, wherein the RF system is a frequency-modulated continuous wave radar system.

4. The inspection system of claim 3, wherein a frequency bandwidth of the continuous wave radar system is in the range of about 1.7 gigahertz (GHz) to about 2.1 gigahertz (GHz).

5. The inspection system of claim 1, wherein at least the RF system is provided on a platform that can be controllably moved in the scan direction, on or adjacent to the surface of the concrete structure.

6. The inspection system of claim 5, wherein the platform is provided on a track system.

7. The inspection system of claim 5, wherein the processor is further configured to control movement of the platform in the scan direction.

8. The inspection system of claim 1, wherein estimating a maximum value at each scan location to estimate reflection amplitude comprises using a spatial resolution; and wherein the processor comprises a synthetic-aperture radar (SAR) sub-system configured to enhance the spatial resolution.

9. The inspection system of claim 1, wherein the RF system is a frequency-modulated pulsed wave radar system.

10. The inspection system of claim 1, wherein correcting attenuation of the radio signals comprises increasing amplitudes of the radio signals based on propagation delay.

11. The inspection system of claim 1, wherein creating an analytical signal for each waveform comprises performing a Hilbert transform on each waveform.

12. The inspection system of claim 1, wherein the first reflection corresponds to a surface reflection from an air/concrete interface.

13. A method for determining the condition of a metal-reinforced concrete structure, comprising:
(a) transmitting radio signals into the interior of the metal-reinforced concrete structure at a plurality of scan locations with a radio frequency (RF) system while moving the RE system in a scan direction with respect to a surface of the metal-reinforced concrete structure; and receiving reflected radio signals; and
(b) processing the reflected radio signals by
normalizing each waveform of the reflected radio signals for unity amplitude,
performing a principal component analysis to remove a first reflection from a first interface of the radio signals to the metal-reinforced, concrete structure,
obtaining a first principal component representative of the transmitted radio signals and using the first principal component to filter each waveform,
correcting attenuation of the radio signals in the metal-reinforced concrete structure,
creating an analytical signal for each waveform,
generating a sub-surface 2D image of the metal-reinforced concrete structure using the magnitude of the waveforms,
projecting the 2D image to the scan direction by estimating a maximum value at each scan location to estimate reflection amplitude,
for each identified peak location, plotting a phase for each waveform, and estimating a slope of the phase prior to and after a metal-reinforcement, wherein the slope corresponds to the physical condition of the reinforcement.

14. The method of claim 13;
the first reflection corresponds to a surface reflection from an air/concrete interface.

15. The method of claim 13, wherein transmitting radio signals comprises continuously transmitting radio signals.

16. The method of claim 15, wherein a frequency bandwidth of the continuous transmitted radio signals is in the range of about 1.7 gigahertz (GHz) to about 2.1 gigahertz (GHz).

17. The method of claim 13, wherein transmitting radio signals comprises transmitting pulsed radio signals.

18. The method of claim 13, wherein estimating a maximum value at each scan location to estimate reflection amplitude comprises using a spatial resolution technique.

* * * * *